(12) United States Patent
Jacquemet et al.

(10) Patent No.: US 11,633,547 B2
(45) Date of Patent: Apr. 25, 2023

(54) PROTECTION DEVICE FOR A NEEDLE

(71) Applicant: Becton Dickinson France, Le Pont de Claix (FR)

(72) Inventors: Malo Jacquemet, Stockholm (SE); Marcus Lundh, Lidingo (SE)

(73) Assignee: Becton Dickinson France, Le Pont de Claix (FR)

( * ) Notice: Subject to any disclaimer, the term of this patent is extended or adjusted under 35 U.S.C. 154(b) by 382 days.

(21) Appl. No.: 16/966,105

(22) PCT Filed: Jan. 28, 2019

(86) PCT No.: PCT/EP2019/051985
§ 371 (c)(1),
(2) Date: Jul. 30, 2020

(87) PCT Pub. No.: WO2019/149655
PCT Pub. Date: Aug. 8, 2019

(65) Prior Publication Data
US 2021/0361882 A1 Nov. 25, 2021

(30) Foreign Application Priority Data

Jan. 31, 2018 (EP) .................................... 18305088

(51) Int. Cl.
*A61M 5/32* (2006.01)
(52) U.S. Cl.
CPC ........ *A61M 5/3219* (2013.01); *A61M 5/3202* (2013.01); *A61M 5/3221* (2013.01); *A61M 2205/0216* (2013.01); *A61M 2207/00* (2013.01)

(58) Field of Classification Search
CPC . A61M 5/3202; A61M 5/3216; A61M 5/3219
See application file for complete search history.

(56) References Cited

U.S. PATENT DOCUMENTS 4,872,552 A * 10/1989 Unger ................. A61M 5/3202
604/110
4,950,249 A * 8/1990 Jagger ................. A61M 5/3216
604/263

(Continued)

FOREIGN PATENT DOCUMENTS

WO 2011129783 A1 10/2011
WO 2015148348 A1 10/2015

*Primary Examiner* — Laura A Bouchelle
(74) *Attorney, Agent, or Firm* — The Webb Law Firm

(57) ABSTRACT

The invention relates to a protection device (1) for a needle (203) of a tip (201) of a drug delivery device (202), comprising: —fixing means (2) for fixing the protection device to said tip, —protective legs (4) capable of transitioning from a first configuration ration in which they cover the needle, to a second configuration in which the needle is exposed, and to a third configuration in which they cover the needle, via pivot links, —removable maintaining means for maintaining the protective legs in their first configuration, —retaining means (9, 10) for retaining the protective legs in their third configuration, said pivot links comprising elastic return means (5) for automatically transitioning the protective legs from their first configuration to their second configuration. The invention also relates to an assembly comprising a drug delivery device and said protection device, and to a method for manufacturing said protection device.

19 Claims, 2 Drawing Sheets

(56) References Cited

U.S. PATENT DOCUMENTS

| | | | |
|---|---|---|---|
| 9,149,584 B2 * | 10/2015 | Harms | A61M 5/3216 |
| 2002/0111581 A1 | 8/2002 | Sasso | |
| 2014/0135713 A1 * | 5/2014 | Domonkos | A61B 17/3496 |
| | | | 29/525 |
| 2017/0106149 A1 | 4/2017 | Clawson | |

* cited by examiner

PROTECTION DEVICE FOR A NEEDLE

CROSS-REFERENCE TO RELATED APPLICATIONS

This application is the United States national phase of International Application No. PCT/EP2019/051985 filed Jan. 28, 2019, and claims priority to European Patent Application No. 18305088.9 filed Jan. 31, 2018, the disclosures of which are hereby incorporated by reference in their entirety.

BACKGROUND OF THE INVENTIONS

The present invention relates to a protection device for a needle of a tip of a drug delivery device.

In the present application, the distal end of a piece or a device is understood to be the end furthest from the hand of the user and the proximal end is understood to be the end closest to the hand of the user. Likewise, in the present application, "distal direction" is understood to be the direction of injection, and "proximal direction" is understood to be the direction opposite the direction of injection.

A drug delivery device such as, for example, a syringe, must be handled with care before and after use due to the presence of a needle. To minimize the risk of accidental injury due to needle sticks, syringes are typically furnished on their needle hub with a needle shield that covers the sharpened tip of the needle. The needle shield is removed prior to use to expose the sharpened tip of the needle. Such a shield also serves to protect the sharpened tip of the needle and to preserve its sterility prior to use of the injection device.

After use, the user must be able to discard the drug delivery device without having to take the risk to be injured by the used needle. A protection device may be used for covering the used needle once the injection is completed. The operation of covering the used needle with the protection device is hazardous. For example, the protection device may be approached towards the distal end of the needle with one hand while the user holds the needle tip with the other hand, and special care must be taken in order to avoid sticking the first hand with the used needle. Indeed, accidental needle sticks at this step must be avoided.

In a view of remedying to this problem, protection devices for a needle of a drug delivery device, where said protection device is capable of ensuring protection of the needle both prior to use and after use, without having to remove the protection device from the drug delivery device, have been proposed. Some of these protection devices may comprise a cap extending upon the needle and capable of pivoting in an open position for giving access to the needle. Nevertheless, these protection devices usually comprise a significant number of components, complex systems and fastidious steps for opening the cap, keeping it open during injection and then closing the cap. These protection devices may consequently occupy a significant volume requiring important storage space. The manufacturing of these protection devices may also require long and complex processes.

There is therefore a need for a protection device capable of protecting the needle of the tip of a drug delivery device prior to use and after use, and that would be simple to use and to manufacture.

In particular, it would be desirable to provide a protection device capable of protecting the needle of the tip of a drug delivery device from ambiant contamination before use while having efficient, and preferably unreleasable, means for protecting the used needle after use.

BRIEF SUMMARY OF THE INVENTION

A first aspect of the invention is to provide a protection device for a needle of a tip of a drug delivery device, providing for a simple and friendly implementation, as well as for a limited number of components, the protection device therefore occupying a limited volume.

A first aspect of the invention is a protection device for a needle of a tip of a drug delivery device, said protection device comprising:

fixing means or a fixing element configured to secure said protection device to the tip of the drug delivery device;

at least two protective legs each connected to said fixing means or fixing element by a pivot link, said protective legs being capable of transitioning from a first configuration in which they cover the needle before use, to a second configuration in which the needle is exposed, and to a third configuration in which they cover the needle after use;

removable maintaining means or a removable maintaining element configured to maintain said protective legs in their first configuration; and retaining means or a retaining element configured to retain said protective legs in their third configuration.

Advantageously, the pivot links comprise elastic return means or an elastic return element configured to automatically transition said protective legs from their first configuration to their second configuration upon removal of said removable maintaining means or said retaining element.

The protection device of the invention is very simple to use and friendly. Before use, the protection device is provided with the protective legs in a first configuration in which they cover the needle. For example, the two or more protective legs extend from the fixing means or fixing element in the distal direction and cover the needle, preferably in a way that allows no access to the needle. The protection device may be provided with two, three, four or more legs, as long as said legs, in combination, globally form an envelope covering the needle in a protective way.

The user simply needs to remove, for example manually, the removable maintaining means or removable maintaining element from the device, and the protective legs automatically transition to their second configuration, in which the needle is exposed, thanks to the elastic return means or elastic return element going from a stressed state to a less stressed state. For example, in their second configuration, the protective legs are open. For example, in their second configuration, each protective leg may extend in a direction secant to the longitudinal axis of the tip. In their second configuration, each protective leg extends preferably perpendicularly and outwardly with respect to the longitudinal axis of the tip and of the needle. The user needs not use his hands in order to open the protective legs by an additional step. Risks of accidental needle sticks are therefore avoided. In addition, the protective legs directly open in a convenient position for the needle to be used in view of proceeding to the injection. The user needs not think it over and take time to open the legs in a correct position; this step is performed automatically, without the user having to intervene.

In said second configuration of the protective legs, the needle is exposed and the injection step may take place. Once the injection is completed, the user may simply position, for example manually, the protective legs back in a configuration, herein after called third configuration, in which they cover the needle and he may then simply activate the retaining means or retaining element for retaining said legs in said third configuration.

The protection device of the invention is therefore particularly simple and friendly to implement. The user needs only performing a limited number of steps. In addition, as will appear from the description below, the protection device of the invention is simple to manufacture and may comprise a limited number of components.

The protection device of the invention is particularly suitable for use with prefilled drug delivery devices.

In embodiments, the elastic return means or elastic return element are configured so as to be in a rest state in said second configuration of said protective legs. For example, the elastic return means or elastic return element are capable of adopting a stressed state, in which they store a mechanical energy, and a rest state, in which said energy has been totally freed and in which said elastic return means or elastic return element are stable. For example, the elastic return means or elastic return element are in their rest state when the protective legs are in their second configuration. As such, the protective legs are therefore in a stable state in their second configuration and the needle remains exposed, without having to use an additional means element, or component for maintaining the protective legs in their second configuration. For example, the elastic return means or elastic return element are in a stressed state in the first and third configurations of the protective legs.

The protection device of the invention is therefore very simple to use. It is also simple to manufacture as there is no need providing the device with an additional maintaining means, element, or component for maintaining the protective legs in their second configuration.

In embodiments, the elastic return means or elastic return element comprise living hinges molded as an integral part with said fixing means or fixing element and said protective legs, wherein said integral part has been molded with said protective legs in their second configuration. Materials suitable for forming such an integral part may be selected from polyethylene, polypropylene, polycarbonate, thermoplastic elastomers and/or combinations thereof. For example, the material may be a combination of polycarbonate and thermoplastic elastomers, or a combination of polypropylene and thermoplastic elastomers. Such a manufacturing process of the fixing means or fixing element, pivot link and protective legs allow obtaining a living hinge capable of deforming from a rest state, which is the state in which it has been molded, to a stressed state, in which it stores energy. When the removable maintaining means or removable maintaining element are removed, the living hinge frees its stored energy and comes back to its state in which it was molded, corresponding to the second configuration of the protective legs. Such embodiments allow manufacturing a protection device with a limited number of components, since the fixing means or fixing element, the pivot link and the protective legs are all formed as a single integral part.

In embodiments, the fixing means or fixing element comprise a collar intended to be mounted onto the tip of the drug delivery device. For example, the collar, the living hinges and the protective legs are all molded together as a single part, with the protective legs being in their second configuration. For example, the material used is selected from polyethylene, polypropylene, polycarbonate, thermoplastic elastomers and/or combinations thereof. For example, the material may be a combination of polycarbonate and thermoplastic elastomers, or a combination of polypropylene and thermoplastic elastomers.

In embodiments, the protection device further comprises an inner casing receiving said needle and a distal end of said tip in a sealing way, for example such that the needle is sealed from ambient contamination, in said first configuration of said protective legs. For example, the inner casing may be accommodated between the needle and the protective legs. The inner casing allows protecting the needle from ambient contamination, thereby ensuring its sterility, in particular before use of the drug delivery device.

In embodiments, the inner casing comprises a needle plug in which a distal end of the needle penetrates. The distal end of the needle is therefore securely protected and risks of needle stick injuries are avoided. In preferred embodiments, the needle plug is made of a soft material allowing the piercing by the distal end of the needle. Suitable materials for forming the needle plug may be selected from rubber, thermoplastic elastomers and combinations thereof. In embodiments, the whole inner casing may be formed of such a soft material like rubber, thermoplastic elastomers and combinations thereof, such material being particularly suitable for forming a sealing line by friction fit engagement on the tip of the drug delivery device.

In embodiments, the removable maintaining means or removable maintaining element comprise a cover surrounding at least part of the protective legs in their first configuration. In such a position, the protective legs extending distally over the needle, the cover maintains the elastic return means or elastic return element, for example the living hinge, in a stressed state. The cover may surround only a part of the protective legs, or the totality of the protective legs, as long as it maintains said legs in their first configuration. The cover may be maintained around said protective legs by any means, element, or component allowing its easy and manual removal by a user.

For example, the cover may be removably engaged with the protective legs by friction fit engagement or peg and cam engagement. For example, the cover may be initially friction fitted onto a distal end of the protective legs and may then further be easily removed from said protective legs by a user pulling said cover in the distal direction. Alternatively or in combination, the cover may be engaged with the protective legs by engagement of a peg located on the cover into a cam located on the protective legs. The cover may then easily be removed by a user pulling the cover in the distal direction, thereby freeing the peg from the cam.

Suitable materials for forming the cover may for example be selected from polyethylene, polypropylene and combinations thereof.

In embodiments, the inner casing is fixed to said cover. For example, the inner casing may be attached to the cover thanks to a protruding part engaging a recess. The cover and the inner casing may also be formed by one of a bi-material co-injection or bi-injection molding process. In such embodiments, the inner casing is removed from the tip of the drug delivery device simultaneously with the removal of the cover. The implementation of the protection device of the invention is therefore not complicated by the presence of the inner casing.

In embodiments, the retaining means or retaining element are selected from snap features, gluing means or glue, peg and cam engagement and combinations thereof, located on one or more protective legs and cooperating together so as to retain said legs in their third configuration. For example, a part of the retaining means or retaining element may be located on a first protective leg, for example on an inner wall of said first protective leg, and a complementary part of said retaining means or retaining element may be located on the second protective leg, for example on an inner wall of said second protective leg. In embodiments where the protection device is provided with more than two legs, a part of the retaining means or retaining element may be located on a first protective leg, for example on an inner wall of said first protective leg, and a complementary part of the retaining means or retaining element may be located on an adjacent protective leg, for example on an inner wall of said adjacent protective leg, so that all the legs, in combination, are maintained in their third configuration, in which they cover the needle. Preferably, the protective legs are configured to form a closed envelope surrounding totally said needle in their third configuration. Access to the used needle is therefore totally prohibited and risks of accidental needle sticks are safely avoided.

In embodiments, the retaining means or retaining element are configured to produce an audible, visible and/or tactile feedback at the time they are activated. The user is therefore ensured that the needle is safely protected.

In preferred embodiments, the retaining means or retaining element are configured so as to retain the protective legs in their third configuration in an unreleasable way. There is therefore no risk that a user deactivates the retaining means or retaining element to regain access to the used needle.

In embodiments, the protection device comprises inhibiting means or inhibiting element configured to inhibit said retaining means or retaining element in said first configuration of said protective legs. Such inhibiting means or inhibiting element allow preventing the protective legs to be inadvertently locked in their first configuration in an unreleasable manner, especially when the retaining means or retaining element are unreleasable retaining means or an unreleasable maintaining element. For example, in embodiments where the retaining means or retaining element comprises snap features located on respective inner walls of the protective legs, the inhibiting means or inhibiting element may comprise an intermediate piece located between the respective inner walls of the protective legs and preventing said snap features to cooperate together in said first configuration of said legs. The intermediate piece may form a temporary mechanical deactivation of the snap features in the first configuration of the protective legs. The inhibiting means or inhibiting element, for example the intermediate piece, may be removed from the protection device before the injection step, and therefore before placing the protective legs in their third configuration.

In embodiments, the intermediate piece is a part of the inner casing. The inner casing may be removed from the protection device before the injection step. In embodiments where the inner casing is fixed to the removable means or the removable element, for example the cover, the inner casing is removed simultaneously with the cover, thereby rendering to the retaining means or retaining element their capacity of being activated when needed, namely after injection.

In embodiments where the retaining means or retaining element comprises glue spread on respective inner walls of said protective legs, the inhibiting means or inhibiting element may comprise removable protective sheets covering said spread glue in said first configuration of said legs. The protective sheets allow preventing the protective legs to stick one to another in their first configuration, so that said legs may be able to transition to their second configuration to allow the injection step to take place. Once the injection is completed, the user may therefore simply pull on the protective sheets so as to remove them from the inner walls of the protective legs, thereby uncovering the spread glue. The user then simply needs to press the protective legs together. The spread glue of each protective leg cooperates with the spread glue of the other protective leg, or of an adjacent leg in case the protection device comprises more than two legs, thereby retaining the protective legs in their third configuration, in which they safely cover the needle.

Another aspect of the present invention is a drug delivery device having a tip provided with a needle further comprising a protection device as above fixed onto said tip.

Another aspect of the present invention is an assembly comprising a drug delivery device having a tip provided with a needle and a protection device as above.

Another aspect of the present invention is a method for manufacturing a protection device as above, comprising the following steps:

Molding as an integral part at least said fixing means or fixing element, said protective legs and said elastic return means or elastic return element in said second configuration of said protective legs;

Providing said integral part with said retaining means or retaining element; and Placing said protective legs in said first configuration and positioning said removable maintaining means or removable maintaining element so as to maintain said protective legs in said first configuration.

In embodiments, the retaining means or retaining element are molded with said integral part.

The manufacturing method of the protection device of the invention is therefore particularly straightforward; it requires a very limited number of steps and may be completed at an industrial scale easily.

According to another aspect of the invention, a protection device for a needle of a tip of a drug delivery device is provided. The protection device includes a fixing element configured to secure said protection device to the tip of the drug delivery device and at least two protective legs each connected to said fixing element by one or more pivot links, said protective legs configured to transition from a first configuration in which the protective legs cover the needle before use, to a second configuration in which the needle is exposed, and to a third configuration in which the protective legs cover the needle after use. The protection device further includes a removable maintaining element configured to maintain said protective legs in the first configuration and a retaining element configured to retain said protective legs in the third configuration. Said pivot links include an elastic return element configured to automatically transition said protective legs from the first configuration to the second configuration upon removal of said removable maintaining element.

According to another aspect of the invention, a drug delivery device is provided. The drug delivery device includes a tip provided with a needle and a protection device including a fixing element configured to secure said protection device to the tip of the drug delivery device and at least two protective legs each connected to said fixing element by one or more pivot links, said protective legs configured to transition from a first configuration in which the protective legs cover the needle before use, to a second configuration in which the needle is exposed, and to a third configuration in which the protective legs cover the needle after use. The protection device further includes a removable maintaining element configured to maintain said protective legs in the first configuration and a retaining element configured to retain said protective legs in the third configuration. Said pivot links include an elastic return element configured to automatically transition said protective legs from the first configuration to the second configuration upon removal of said removable maintaining element.

According to another aspect of the invention, a method for manufacturing a protection device is provided. The protection device includes a fixing element configured to secure said protection device to the tip of the drug delivery device and at least two protective legs each connected to said fixing element by one or more pivot links, said protective legs configured to transition from a first configuration in which the protective legs cover the needle before use, to a second configuration in which the needle is exposed, and to a third configuration in which the protective legs cover the needle after use. The protection device further includes a removable maintaining element configured to maintain said protective legs in the first configuration and a retaining element configured to retain said protective legs in the third configuration. Said pivot links include an elastic return element configured to automatically transition said protective legs from the first configuration to the second configuration upon removal of said removable maintaining element. The method includes molding as an integral part at least said fixing element, said protective legs, and said elastic return element in said second configuration of said protective legs, providing said integral part with said retaining element, placing said protective legs in said first configuration and positioning said removable maintaining element so as to maintain said protective legs in said first configuration

BRIEF DESCRIPTION OF THE DRAWINGS

The invention will now be described in details, with reference to the enclosed drawings in which.

DETAILED DESCRIPTION OF THE INVENTION

Figure 1:
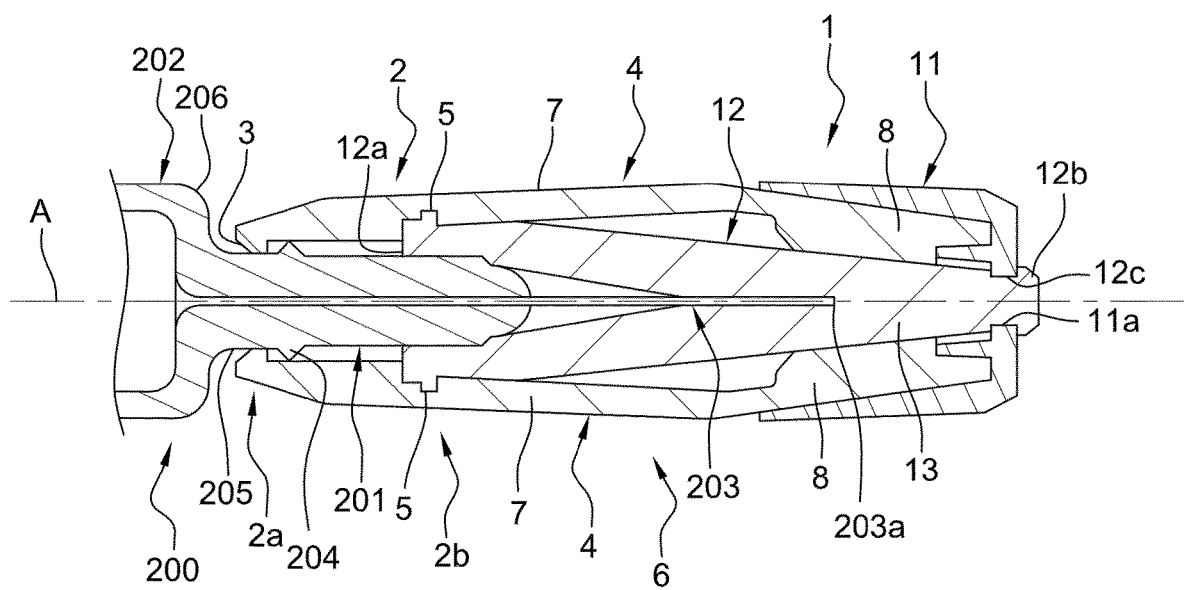
FIG. 1 is a longitudinal cross section view of a first embodiment of the protection device of the invention in the first configuration of the protective legs.

With reference to FIG. 1 is shown an embodiment of a protection device 1 of the invention, in a before use position. As will appear from the below description, the protection device preferably comprises an outer casing comprising a collar, legs and hinges, an inner casing and a cover.

In FIG. 1, the protection device 1 is mounted onto the tip 201 of a drug delivery device 200, by means of fixing means or by a fixing element, a collar 2 on the example shown. The collar 2 secures the protection device 1 to the tip 201 of the drug delivery device 200 in a non removable manner. Indeed, the protection device 1 of the invention is intended to remain fixed to the tip 201 of the drug delivery device 200 during all the time of its use, namely before use of the drug delivery device 200, during the injection step, and after use of the drug delivery device 200. The protection device 1 of the invention is therefore intended to protect the user from accidental needle sticks before and after use of the drug delivery device 200, without the user having to remove the protection device from the tip 201 of the drug delivery device 200 for proceeding to the injection step.

The drug delivery device 200 is provided with a barrel 202, a tip 201 and a needle 203, fixed at a distal end of the tip 201. The needle 203 has a sharpened distal end 203a. On the example shown, the tip 201 of the drug delivery device 200 is provided on its outer wall with an annular ridge 204 forming an annular groove 205 with the shoulder 206 of the barrel 202.

As appears from FIG. 1, the collar 2 of the protection device 1 comprises at its proximal end 2a an inner radial rim 3 which is engaged into the annular groove 205 of the tip 201 so as to maintain the protection device 1 fixed to the tip 201.

In embodiments not shown, the collar could be fixed to the tip of the drug delivery device by any other fixing means or fixing element: for example, the collar could be glued to the tip of the drug delivery device.

The collar may be formed in a single piece or in two pieces. For example, the collar may comprise an inner ring glued or snapped on the tip of the drug delivery device and an outer ring surrounding at least partially the inner ring.

The protection device 1 further comprises at least two protective legs 4, each protective leg 4 being connected to a distal end 2b of the collar 2 by means of a pivot link, under the form of or including a living hinge 5 on the example shown.

Figure 2:
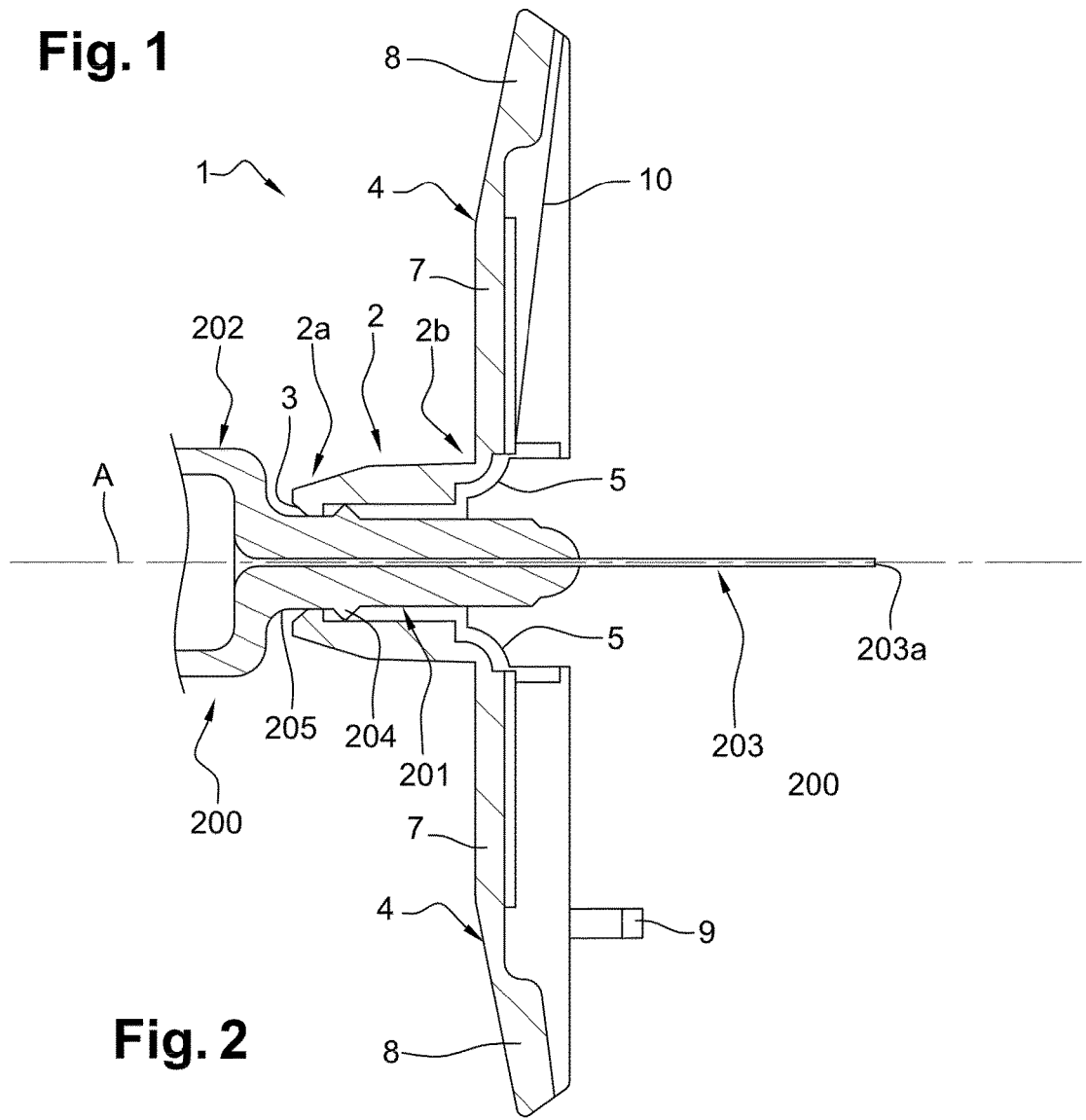
FIG. 2 is a longitudinal cross section view of the protection device of FIG. 1 in the second configuration of the protective legs.
Figure 3:
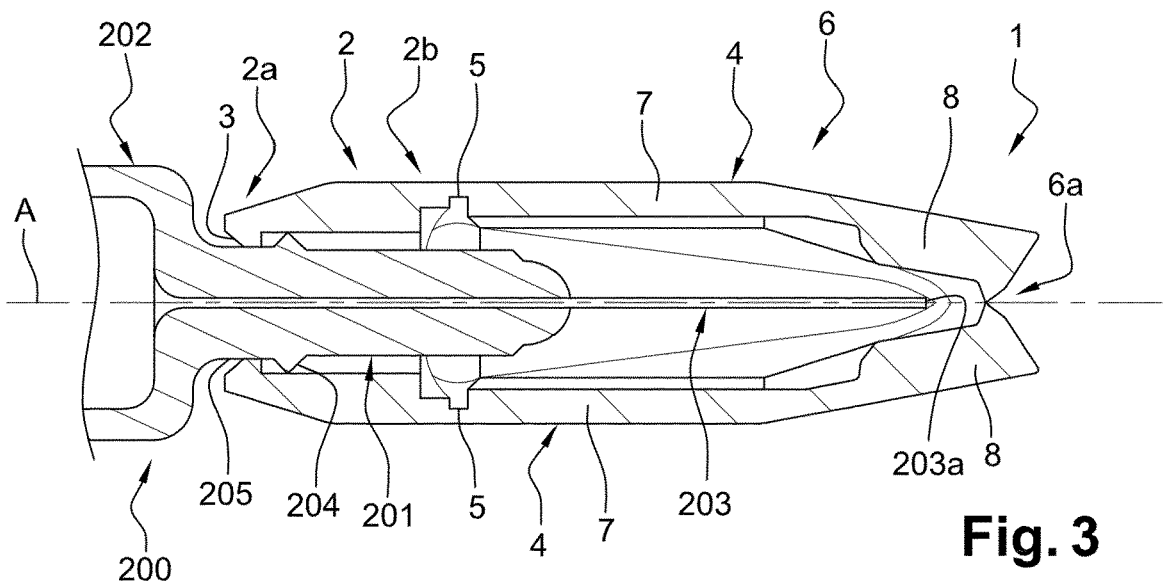
FIG. 3 is a longitudinal cross section view of the protection device of FIG. 1 in the third configuration of the protective legs.

As will appear from the description below, the protective legs 4 are capable of transitioning from a first configuration in which they cover the needle 203 before use as shown in FIG. 1, to a second configuration in which the needle 203 is exposed as shown in FIG. 2, and to a third configuration in which they cover the needle 203 after use as shown in FIG. 3.

In their first and third configurations, as shown in FIGS. 1 and 3, the protective legs 4 are intended to cover the needle 203 in order to protect a user from accidental needle sticks.

In this view, the protective legs 4 preferably show a shape that allows them to form an envelope 6 surrounding the needle 203 when they are combined together either in their first configuration or third configuration. In such configurations, the protective legs 4 extend distally from the living hinge 5 up to at least the distal end 203a of the needle 203.

In the example shown, the protection device 1 being provided with two legs 4, each leg 4 shows the global shape of a semi-cylinder 7. The semi-cylinder may have a tapering distal part 8 capable of rejoining the tapering distal part 8 of the semi-cylinder 7 of the other leg 4 so as to close the distal end of the thus formed envelope 6 (see FIG. 3). In this view, with reference to FIG. 2, one of the protective legs 4 is provided with a notch 9 capable of being engaged in an abutment 10 of the other protective leg 4 so as to retain the two protective legs 4 in their third configuration, as shown in FIG. 3.

In the first configuration of the protective legs 4 of the example shown in FIG. 1, the tapering distal parts 8 of the two legs are not joined, since the distal closure of the envelope 6 formed by the two legs 4 is performed in another way, as will be explained in the description below. With reference to FIG. 3 nevertheless, it can be seen that the tapering distal parts 8 of the semi-cylinder 7 are joined to close the distal end 6a of the envelope 6 surrounding the needle 203.

In embodiments not shown, the protection device could be provided with more than two legs, such as three or four legs, as long as when combined together either in their first configuration or third configuration, the legs provide for an envelope surrounding the needle, preferably closed at its distal end.

With reference to FIG. 1, the protection device 1 further comprises a cover 11 closing the distal end of the envelope 6 formed by the two protective legs 4 in their first configuration. The cover 11 has the global shape of a cap and surrounds the distal regions, for example the tapering distal parts 8, of the protective legs 4.

The protection device further comprises an inner casing 12. The inner casing is receiving the needle 203. The inner casing preferably has an open proximal end 12a and a closed distal end 12b. The inner casing 12 is mounted onto the tip 201 of the drug delivery device 200 by friction fit engagement of an inner wall of its proximal end 12a on a distal end of the outer wall of the tip 201 of the drug delivery device 200. The proximal end of the inner casing is preferably inserted between the tip of the drug delivery device and the outer casing. The inner casing 12 receives the needle 203 and the distal end of the tip 201 in a sealing way. The needle 203 is therefore protected from ambient contamination. On the example shown, the distal part of the inner casing 12 forms a plug 13, preferably made from a soft and deformable material, into which the distal end 203a of the needle 203 penetrates. The sharpened distal end 203a of the needle 203 is therefore safely covered and accidental needle sticks may be safely avoided.

The inner casing 12 is usually made entirely from a soft and deformable material. Suitable materials for forming the inner casing 12 may be selected from rubber, thermoplastic elastomers and/or combinations thereof.

On the example of FIG. 1, the inner casing 12 is attached to the cover 11. For example, the cover 11 is provided with a protruding part 11a engaged in a recess 12c of the inner casing 12.

In embodiments not shown, the cover may not include any inner casing, the needle 203 being simply received in the envelope formed by the combination of the two protective legs 4 in their first configuration, for example closed at its distal end by the cover 11.

With reference to FIG. 1, the cover 11 maintains the two protective legs 4 in their first configuration, for example by applying a stress onto the living hinges 5, or on the protective legs 4.

The living hinges 5 of the protection device 1 are configured so as to be able to store a mechanical energy in a stressed state and to free this energy by coming back to a less stressed state, for example to a rest state, thereby acting as an elastic return element or elastic return means. On the example shown, the living hinges 5 are particularly configured so as to be in a rest state in the second configuration of the protective legs 4, and to be able to store energy in a stressed state, namely in the first or third configuration of the protective legs 4.

In this view, the living hinges 5 have been molded as an integral part with the collar 2 and the protective legs 4, with the protective legs 4 in their second configuration, as shown in FIG. 2, namely extending substantially perpendicularly with respect to a longitudinal axis A of the collar 2. The rest state of the living hinges 5 therefore correspond to their state as shown in FIG. 2, in which the living hinges 5 form a right angle with respect to the longitudinal axis A.

On the contrary, with respect to FIGS. 1 and 3, the living hinges 5 are aligned on the longitudinal axis A and are therefore in a stressed state. With respect to FIG. 1, the living hinges 5 are maintained in a stressed state by means of the cover 11 maintaining the protective legs 4 in their first configuration. With respect to FIG. 3, the living hinges 5 are maintained in a stressed state by means of the notch 9 engaged in abutment 10 (see FIG. 2) thereby retaining the protective legs 4 in their third configuration.

Suitable materials for molding the collar 2, the living hinges 5 and the protective legs 4 as an integral part may be selected from polyethylene, polypropylene, polycarbonate, thermoplastic elastomers and/or combinations thereof.

The manufacturing process of the protection device of the invention is therefore particularly simple. No additional maintaining means, element, or component is necessary for maintaining the protective legs 4 in their second configuration.

For example, the protection device 1 of FIGS. 1-3 may be manufactured as follows: the collar 2, the living hinges 5, the protective legs 4 with the notch 9 and the abutment 10 may be molded as an integral part from a suitable material such as polypropylene, polycarbonate, thermoplastic elastomers and/or combinations thereof, with the protective legs 4 positioned in their second configuration. The protective legs 4 are then progressively refolded toward each other while the cover 11 and the inner casing 12 are proximally approached and positioned as shown in FIG. 1 so as to maintain the protective legs 4 in their first configuration.

The use of the protection device 1 of the invention will now be described with reference to FIGS. 1-3.

The protection device 1 is provided as shown in FIG. 1, mounted onto the tip 201 of a drug delivery device 200 filled with a product to be injected (not shown). The protective legs 4 are in their first configuration: they extend distally from the living hinges 5 and form an envelope 6 surrounding the needle 203. The envelope 6 is closed at its distal end by the distal end 12b of the inner casing 12 and the protective legs 4 are maintained in their first configuration by the cover 11 being friction fitted onto their distal tapering parts 8. The living hinges 5 are therefore aligned with the longitudinal axis A and are in a stressed state. The distal end 203a of the needle 203 is embedded into the plug 13 of the inner casing 12. The inner casing 12 seals the needle 203 against contamination. The notch 9 is prevented from engaging the abutment 10 by means of the inner casing 12 being interposed between said two protective legs 4.

Before use, the protection device 1 of FIGS. 1-3 therefore protects the needle 203 from ambient contamination on one hand, and the user on the other hand.

In order to proceed with the injection, the user removes the cover 11 by pulling distally on the cover 11. The inner casing 12 is attached to the cover and is then removed together with the cover 11. The stress exerted by the cover 11 on the protective legs 4 and therefore on the living hinges 5 is therefore released and the living hinges 5 come naturally and automatically to their rest state, namely in a configuration in which the needle is uncovered. According to one embodiment, in this configuration, the protective legs 4 may form a right angle with the longitudinal axis A. The protective legs 4 are by consequence automatically placed in their second configuration, in which they extend perpendicularly with respect to the longitudinal axis A, thereby exposing the needle 203, as shown in FIG. 2.

The user may then easily proceed to the injection, without having to manually move the protective legs 4 in any specific position. In addition, the user does not need to activate any maintaining means, element, or component for keeping the protective legs 4 in the correct position during the injection step. Indeed, thanks to the living hinges 5 being in their rest state in the second configuration of the protective legs 4, the user knows that the protective legs 4 will remain in a stable position during the time of the injection step.

Once the injection step is completed, the user simply refolds the two protective legs 4 together until the notch 9 engages the abutment 10, so as to put the protective legs 4 in their third configuration, as shown in FIG. 3, in which they again cover the needle 203. Since the inner casing 12 is no more present, the protective legs 4 are now able to come closer to one another and to close the distal end 6a of the envelope 6 they form, particularly with their distal tapering parts 8 rejoining one another.

In addition, as a help to the user, the notch 9 may produce an audible, visual and/or tactile feedback at the time it engages the abutment 10.

The user is therefore protected from the distal end 203a of the used needle 203. Accidental needle sticks are safely avoided and the user may discard the protection device 1 and drug delivery device 200.

As can be seen from these description and figures, the protection device 1 comprises a limited number of components and occupies a limited volume. It is also very simple to use and to manufacture.

As clear from the above example, the notch 9 and abutment 10 form efficient, preferably unreleasable, retaining means for locking the protective legs 4 in their third configuration and consequently protecting the used needle after use of the drug delivery device 200, while the inner casing 12 forms inhibiting means to inhibit these retaining means (notch 9 and abutment 10) in the first configuration of the protective legs 4. The protective legs 4 are maintained in their first configuration thanks to the cover 11, which forms removable maintaining means different from the retaining means.

Figure 4:
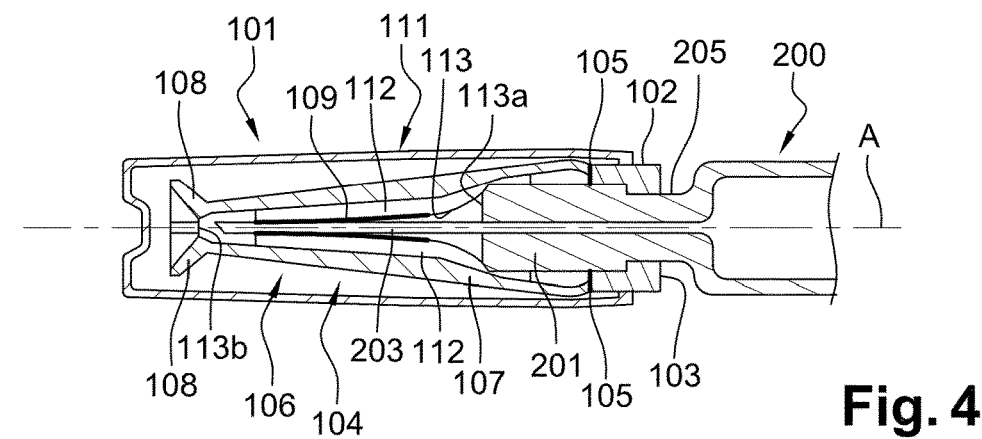
FIG. 4 is a longitudinal cross section view of a second embodiment of the protection device of the invention in the first configuration of the protective legs.
Figure 5:
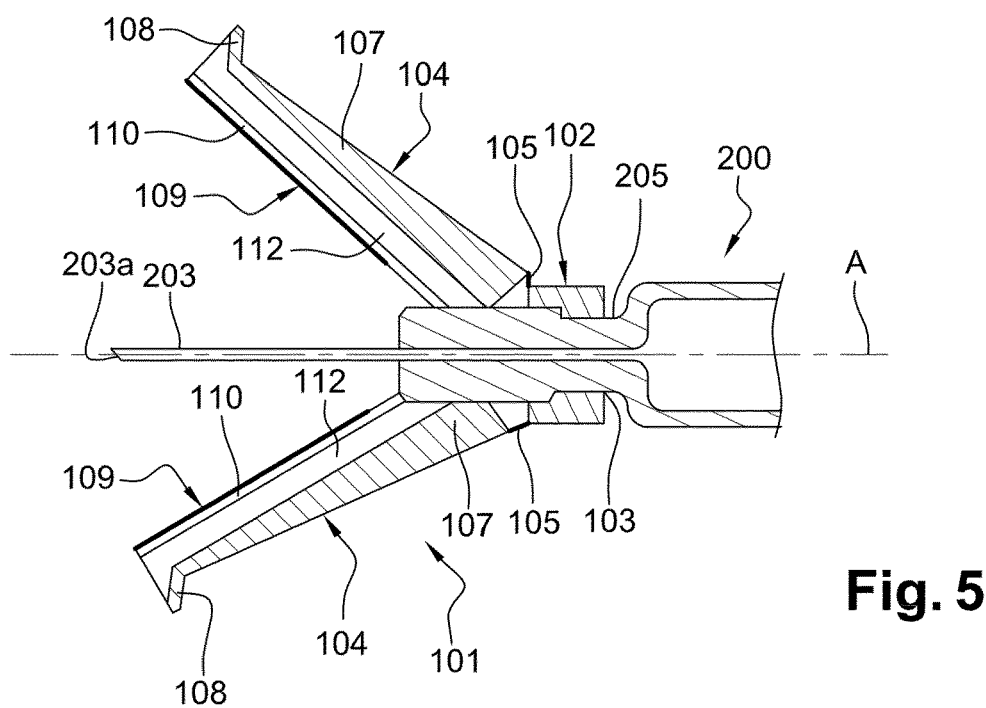
FIG. 5 is a longitudinal cross section view of the protection device of FIG. 4 in a position where the protective legs are in the process of transitioning from their first configuration to their second configuration.

With respect to FIGS. 4 and 5 is shown another embodiment of a protection device 101 of the invention, in which the retaining means or retaining element comprises glue spread on inner walls of the protective legs.

The protection device 101 of FIGS. 4 and 5 comprises a collar 102 and two protective legs 104, each protective leg 104 being connected to the collar 102 by living hinges 105.

The collar 102 is fixed to the tip 201 of the drug delivery device 200, for example by means of an inner ring 103 of said collar 102 engaged in an annular groove 205 of the tip 201.

Each protective leg 104 has a shape of a semi-cylinder 107. Each protective leg may also have a flared out distal part 108 capable of rejoining the flared out distal part 108 of the other leg 104 so as to close the distal end of the thus formed envelope 106, as shown in FIG. 4.

Each protective leg 104 is provided on its inner wall with a layer 112 of soft material, the combination of the two layers 112 in the first configuration of the protective legs 104 forming or defining an inner casing 113 tightly enclosing the needle 203. The resulting proximal end 113a of the inner casing 113 is mounted in a sealing way on the tip 201 of the drug delivery device 200 and the resulting distal end 113b of the inner casing 113 extends beyond the distal end 203a of the needle 203. The needle 203 is therefore received in the inner casing 113 in a sealing way and is protected from ambient contamination.

The soft material may be selected from rubber, elastomers and combinations thereof.

Each layer 112 of soft material is provided, at least in its distal part, with a layer of spread glue 110 covered by a removable protective sheet 109 in the first configuration of the protective legs 104.

With respect to FIG. 4, the protection device 101 is provided with a cover 111 surrounding the two protective legs 104 in their first configuration. On the example shown, the cover 111 has the global shape of an elongate cap surrounding the protective legs 104 on their whole length, a distal end 111a of the cover 111 being friction fitted onto the collar 102 and the living hinges 105.

Like for the embodiment of FIGS. 1-3, the living hinges 105 have been molded as an integral part with the collar 102 and the protective legs 104, with the protective legs in their second configuration, thereby forming or defining an outer casing. As a result, the living hinges 105 are in a stressed state in the first configuration of the protective legs 104 and in a rest state in the second configuration of the protective legs 104.

For example, the protection device 101 of FIGS. 4 and 5 may be manufactured as follows: the collar 102, the living hinges 105 and the protective legs 104 may be molded as an integral part from a suitable material such as polypropylene, polycarbonate, thermoplastic elastomers and/or combinations thereof, with the protective legs 104 positioned in their second configuration. A layer 112 of soft material may then be applied on the inner wall of each protective leg 104. A certain amount of glue 110 may then be spread at least in a distal part of said layers 112 and protective sheets 109 may be applied so as to cover the spread glue 110.

The protection device 101 of FIGS. 4 and 5 may be used as follows: the protection device 101 is provided as shown in FIG. 4, mounted onto the tip 201 of the drug delivery device 200 filled with a product to be injected (not shown). The protective legs 104 are in their first configuration: they extend distally from the living hinges 105 and form an envelope 106 surrounding the needle 203. The cover 111 is friction fitted onto the collar 102 and onto the living hinges 105, thereby maintaining the living hinges 105 in a stressed state and the protective legs 104 in their first configuration. The needle 203 is tightly enclosed within the inner casing 113 resulting from the combination of the layers 112 of soft material. The inner casing 113 seals the needle 203 against contamination. The spread glue 110 of each layer 112 of soft material is prevented from contacting the spread glue of the other protective leg 104 by means of the protective sheets 109.

Before use, the protection device 101 therefore protects the needle 203 from ambient contamination and further protects the user from accidental needle sticks.

In order to proceed with the injection, the user removes the cover 111 by pulling it in the distal direction. The stress exerted by the cover 111 on the living hinges 105 is therefore released and the living hinges 105 come naturally and automatically to their rest state, namely in the configuration in which they form a right angle with the longitudinal axis A. The protective legs 104 are by consequence automatically placed in their second configuration, in which they may extend for example of an angle of 90° with respect to the longitudinal axis A, thereby exposing the needle 203. FIG. 5 shows the protection device 101 in an intermediate position in which the protective legs 104 are transitioning from their first configuration to their second configuration (not shown).

The user may then easily proceed to the injection, without having to manually move the protective legs 104 in any specific position. Thanks to the living hinges 105, the user knows that the protective legs 104 are readily correctly positioned. In addition, the user does not need to activate any maintaining means or maintaining element for keeping the protective legs 104 in the correct position during the injection step. Indeed, thanks to the living hinges 105 being in their rest state in the second configuration of the protective legs 104, the user knows that the protective legs 104 will remain in a stable position during the time of the injection step.

Once the injection is completed, the user simply removes the protective sheets 109 from the inner walls of the protective legs 104, thereby uncovering the glue 110 spread on the layers 112 of soft material. He then refolds the two protective legs 104 and exerts a pressure so as to stick the two protective legs 104 together by contacting the glue 110 spread on the layers 112. The protective legs 104 are then in a third configuration (not shown) in which they form a closed envelope surrounding the needle 203.

As clear from the above example, the glue 110 forms efficient, preferably unreleasable, retaining means for locking the protective legs 104 in their third configuration and consequently protecting the used needle after use of the drug delivery device 200, while the protective sheets 109 form inhibiting means to inhibit these retaining means (glue 110) in the first configuration of the protective legs 104. The protective legs 104 are maintained in their first configuration thanks to the cover 111, which forms removable maintaining means different from the retaining means.

In another embodiment not shown, the glue could be spread on the layer of soft material of one protective leg only.

The user is therefore protected from the distal end 203a of the used needle 203. Accidental needle sticks are safely avoided and the user may discard the protection device 101 and drug delivery device 200.

The protection device 101 comprises a limited number of components and occupies a limited volume. It is also very simple to use and to manufacture.

The protective legs 104 are then progressively refolded toward each other while the cover 111 is proximally approached and positioned as shown in FIG. 4 so as to maintain the protective legs 104 in their first configuration.

The invention is of course not limited to the embodiments described above as examples, but encompasses all technical equivalents and alternatives of the means described as well as combinations thereof.

The protection device of the invention allows providing a device for protecting the needle of a tip of a drug delivery device before injection and after injection, without having to remove the device from the tip of the drug delivery device during the injection step. Moreover, the protection device of the invention is very simple to use and to manufacture. It requires only a limited number of components and occupies a small volume allowing it to be stored while already mounted onto the tip of the drug delivery device.

The invention claimed is:

1. A protection device for a needle of a tip of a drug delivery device, said protection device comprising:
    a fixing element configured to secure said protection device to the tip of the drug delivery device;
    at least two protective legs each connected to said fixing element by one or more pivot links, said protective legs configured to transition from a first configuration in which the protective legs cover the needle before use, to a second configuration in which the needle is exposed, and to a third configuration in which the protective legs cover the needle after use;
    a removable maintaining element configured to maintain said protective legs in the first configuration;
    a retaining element configured to retain said protective legs in the third configuration; and
    inner casing receiving said needle and a distal end of said tip, such that the needle is sealed from ambient contamination, in said first configuration of said protective legs,
    wherein said pivot links comprise an elastic return element configured to automatically transition said protective legs from the first configuration to the second configuration upon removal of said removable maintaining element.

2. The protection device according to claim 1, wherein said elastic return element is configured so as to be in a rest state in said second configuration of said protective legs.

3. The protection device according to claim 1, wherein said elastic return element comprises a living hinge molded as an integral part with said fixing element and said protective legs, wherein said integral part is molded with said protective legs in the second configuration.

4. The protection device according to claim 3, wherein materials forming said integral part are selected from polyethylene, polypropylene, polycarbonate, thermoplastic elastomers, or combinations thereof.

5. The protection device according to claim 1, wherein said fixing element comprises a collar configured to be mounted onto the tip of the drug delivery device.

6. The protection device according to claim 1, wherein said inner casing comprises a needle plug in which a distal end of said needle penetrates.

7. The protection device according to claim 1, wherein said removable maintaining element comprises a cover surrounding at least part of said protective legs in the first configuration, said cover thereby maintaining said elastic return element in a stressed state.

8. The protection device according to claim 7, wherein said cover is removably engaged with said protective legs by friction fit engagement or peg and cam engagement.

9. The protection device according to claim 7, wherein said inner casing is fixed to said cover.

10. The protection device according to claim 1, wherein said retaining element is selected from snap features, glue, peg and cam engagement, andcombinations thereof, located on one or more of the protective legs and cooperating together so as to retain said protective legs in the third configuration.

11. The protection device according to claim 1, further comprising an inhibiting element configured to inhibit said retaining element in said first configuration of said protective legs.

12. The protection device according to claim 11, wherein said retaining element comprises snap features located on respective inner walls of said protective legs,
    wherein said inhibiting element comprises an intermediate piece located between said respective inner walls of said protective legs and preventing said snap features to cooperate together in said first configuration of said legs.

13. The protection device according to claim 12, further comprising an inner casing receiving said needle and a distal end of said tip, such that the needle is sealed from ambient contamination, in said first configuration of said protective legs,
    wherein said intermediate piece is a part of said inner casing.

14. The protection device according to claim 11, wherein said retaining element comprises glue spread on respective inner walls of said protective legs, wherein said inhibiting element comprises removable protective sheets covering said spread glue in said first configuration of said legs.

15. The protection device according to claim 1, wherein said protective legs are configured to form a closed envelope surrounding said needle in the third configuration.

16. A drug delivery device having a tip provided with a needle, the drug delivery device further comprising:
a protection device according to claim 1 fixed onto said tip.

17. An assembly comprising a drug delivery device having a tip provided with a needle and a protection device according to claim 1.

18. A method for manufacturing a protection device according to claim 1, the method comprising:
molding as an integral part at least said fixing element, said protective legs, and said elastic return element in said second configuration of said protective legs;
providing said integral part with said retaining element; and
placing said protective legs in said first configuration and positioning said removable maintaining element so as to maintain said protective legs in said first configuration,
wherein said retaining element is molded with said integral part.

19. A protection device for a needle of a tip of a drug delivery device, said protection device comprising:
a fixing element configured to secure said protection device to the tip of the drug delivery device;
at least two protective legs each connected to said fixing element by one or more pivot links, said protective legs configured to transition from a first configuration in which the protective legs cover the needle before use, to a second configuration in which the needle is exposed, and to a third configuration in which the protective legs cover the needle after use;
a removable maintaining element configured to maintain said protective legs in the first configuration;
a retaining element configured to retain said protective legs in the third configuration; and
inhibiting element configured to inhibit said retaining element in said first configuration of said protective legs,
wherein said pivot links comprise an elastic return element configured to automatically transition said protective legs from the first configuration to the second configuration upon removal of said removable maintaining element.

* * * * *

UNITED STATES PATENT AND TRADEMARK OFFICE
CERTIFICATE OF CORRECTION

PATENT NO. : 11,633,547 B2
APPLICATION NO. : 16/966105
DATED : April 25, 2023
INVENTOR(S) : Malo Jacquemet et al.

It is certified that error appears in the above-identified patent and that said Letters Patent is hereby corrected as shown below:

In the Claims

Column 14, Line 42, Claim 10, delete "andcombinations" and insert -- and combinations --

Signed and Sealed this
Twentieth Day of June, 2023

Katherine Kelly Vidal
*Director of the United States Patent and Trademark Office*